United States Patent [19]
Sherry et al.

[11] Patent Number: 5,951,473
[45] Date of Patent: Sep. 14, 1999

[54] DETERMINATION OF INTRACELLULAR SODIUM AND POTASSIUM IONS BY NMR

[75] Inventors: A. Dean Sherry, Dallas; Navin Bansal, Coppell; Craig R. Malloy, Dallas, all of Tex.

[73] Assignee: Board of Regents, The University of Texas System, Austin, Tex.

[21] Appl. No.: 08/881,756

[22] Filed: Jun. 24, 1997

Related U.S. Application Data

[63] Continuation of application No. 08/248,082, May 24, 1994, abandoned.

[51] Int. Cl.[6] .................................................. A61B 5/055
[52] U.S. Cl. ............................................ 600/420; 424/9.3
[58] Field of Search .............................. 128/653.2, 653.4; 424/9.3, 9.37; 600/410, 419, 420

[56] References Cited

U.S. PATENT DOCUMENTS 5,303,705   4/1994   Nenov ................................... 128/653.2

OTHER PUBLICATIONS

Bansal et al., "In Vivo Na–23 MR Imaging and Spectroscopy of Rat Brain during TmDOTP$^{5-}$ Infusion$^1$," *JMRI*, 2(4):385–392, 1992.

Boulanger et al., "Monitoring of the Effects of Dysprosium Shift Reagents on Cell Suspensions," *NMR in Biomedicine*, 5:1–10, 1992.

Buster et al., "Tm(DOTP)$^{5-}$:A $^{23}$Na$^+$Shift Agent for perfused Rat Hearts," *Magnetic Resonance in Medicine*, 15:25–32, 1990.

Dowd and Gupta, "Multinuclear NMR Studies of Intracellular Cations in Perfused Hypertensive Rat Kidney," *The Journal of Biological Chemistry*, 267(6):3637–3643, 1992.

Foy and Burstein, "Interstitial sodium nuclear magnetic resonance relaxation times in perfused hearts," *Biophys. J.*, 58:127–132, 1990.

Hutchison et al.., "Evaluation of the Double–quantum Filter for the Measurement of Intracellular Sodium Concentration," *The Journal of Biological Chemistry*, 265(26):15506–15510, 1990.

Hutchison and Shapiro, "Measurement of Intracellular Sodium with NMR Methods," *Concepts in Magnetic Resonance*, 3:215–236, 1991.

Kaufman and Horton, "Burn–induced alterations in cardiac β–adrenergic receptors," *Am. J. Physiol.*, 262:H1585–H1591, 1992.

Kohler et al., "In Vivo Sodium Chemical Shift Imaging," *Magnetic Resonance in Medicine*, 23:77–88, 1992.

Lyon et al., "Double–Quantum Surface–Coil NMR Studies of Sodium and Potassium in the Rat Brain," *Magnetic Resonance in Medicine*, 18:80–92, 1991.

Malloy et al. , "Influence of Global Ischemia on Intracellular Sodium in the Perfused Rat Heart," *Magnetic Resonance in Medicine*, 15:33–44, 1990.

Ramasamy et al., "Effects of Negatively Charged Shift Reagents on Red Blood Cell Morphology, Li Transport, and Membrane Potential," *Inorg. Chem.*, 29:3979–3985, 1990.

Rooney and Springer, "The Molecular Environment of Intracellular Sodium: $^{23}$Na NMR Relaxation," *NMR in Biomedicine*, 4:227–245, 1991.

*Primary Examiner*—Ruth S. Smith
*Attorney, Agent, or Firm*—Arnold, White & Durkee

[57] ABSTRACT

New methods for rapid, noninvasive determination of sodium ion in vivo are described. The methods are useful for assessing liver and other organ injury based on a nuclear magnetic resonance determination of intracellular and extracellular sodium in the damaged tissue. A shift reagent, TmDOTP$^{5-}$, is used in vivo to produce baseline resolved peaks of $^{23}$Na. Excellent results are achieved with significantly less TmDOTP$^{5-}$ than with other conventional $^{23}$Na shift reagents such as DyTTHA$^{3-}$. In contrast to use in isolated perfused heart tissue, TmDOTP$^{5-}$ solutions are employed in vivo without added calcium ion. The method has been applied to animal burn models. Results show that intracellular sodium ion levels are dramatically increased, thus providing a rapid assessment of liver function. Similar methods may be applied to the determination of intra- and extracellular potassium ion.

8 Claims, 7 Drawing Sheets

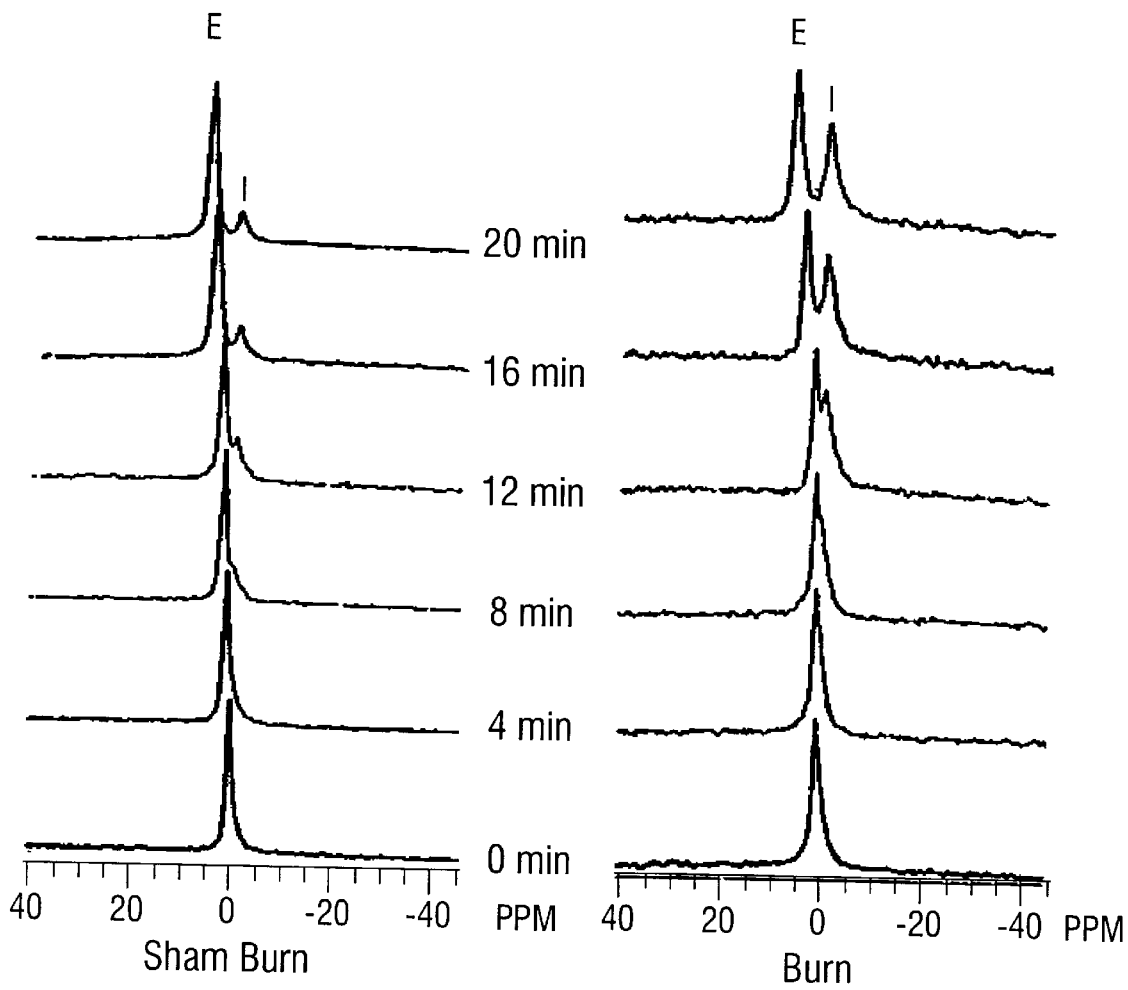
FIG. 5A  Sham Burn
FIG. 5B  Burn

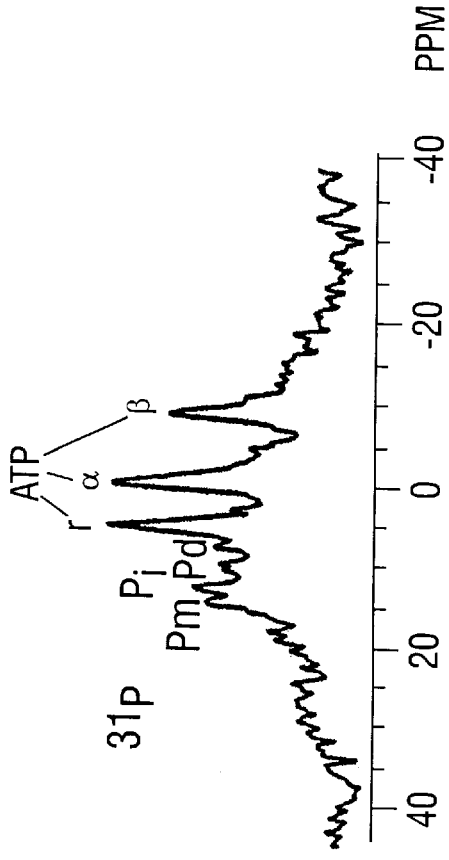
FIG. 6A
FIG. 6B
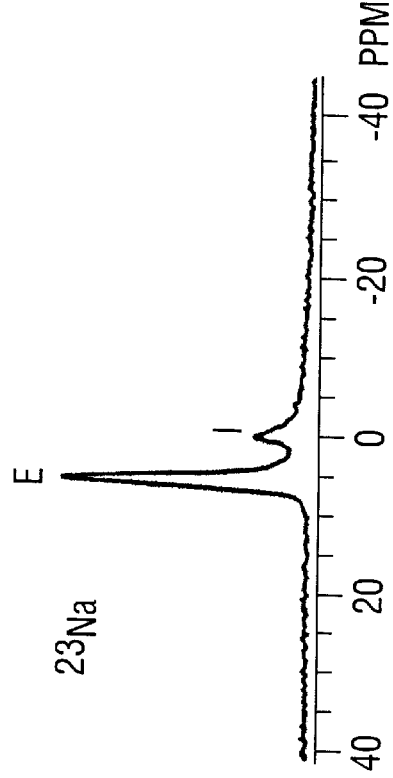
FIG. 6C
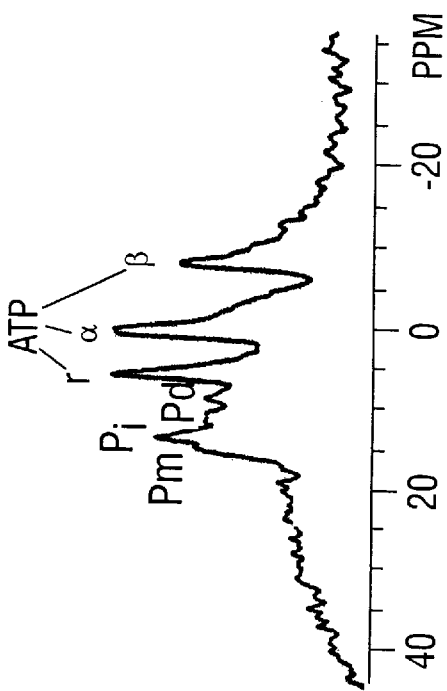
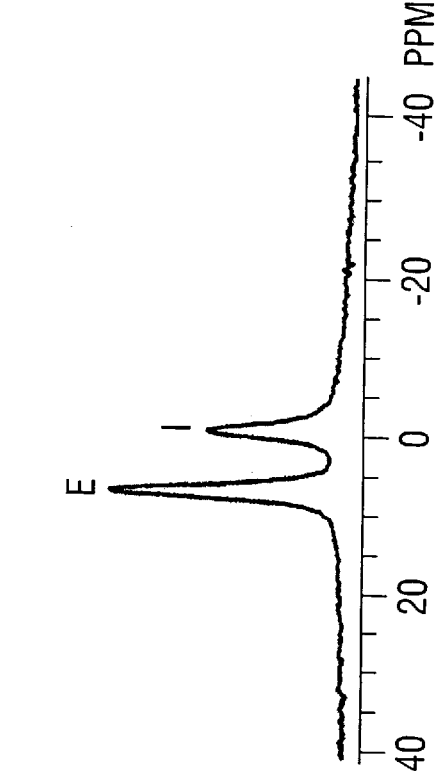
FIG. 6D

DETERMINATION OF INTRACELLULAR SODIUM AND POTASSIUM IONS BY NMR

This application is a continuation of application Ser. No. 08/248,082, filed May 24, 1994 now abandoned.

The U.S. Government has rights in the present invention pursuant to the terms of Grant No. HL-34557, SCOR HL-17669 awarded by the National Institutes of Health and a grant from the Department of Veterans Affairs.

BACKGROUND OF THE INVENTION

1. Field of the Invention

The invention concerns methods of determining tissue injury using non-invasive in vivo determination of intracellular and extracellular sodium and potassium ions by nuclear magnetic resonance procedures.

2. Description of Related Art

Proper therapy for numerous clinical conditions depends on early detection of metabolic abnormalities in a tissue. Perfused tissue and animal studies indicate that intracellular sodium may provide a sensitive and specific indication of the injury; however, measurement of intracellular sodium is neither simple nor quickly performed under currently available protocols. A simple, rapid and noninvasive method of detecting intracellular sodium in a target tissue has yet to be developed.

The sodium ion gradient across the cell membrane is critically important to many cell functions and is sensitive to disease; consequently, there is a continuing interest in methods which differentiate sodium in various tissue compartments. Although nuclear magnetic resonance (NMR) is a convenient, relatively sensitive, nondestructive method for detecting sodium in biological tissue, the usual one-pulse measurement suffers from the fact that $^{23}$Na or $^{39}$K resonances from various tissue compartments are isochronous and hence ion concentration gradients and ion fluxes cannot be monitored.

Likewise, potassium ion gradients, if disrupted, may adversely affect transport across the cell membrane. Transport processes are driven by ATP hydrolysis to generate electrochemical gradients across the membrane. In vivo differences between extra and intracellular potassium ion concentrations may possibly be an indicator of metabolic injury; however, as with sodium ion, NMR methods have not provided an effective means to measure and monitor potassium ion concentrations in the different compartments.

At least three NMR methods have been proposed to solve this problem: (i) methods based on relaxation time differences Lee, H. J., Labadie, C. & Springer, C. S. (1992) *Abstr.* 11th Mtg. SMRM, 2214 ; (ii) multiple quantum filters (MFQ's) Lyon, R. C., Pekar, J., Moonen, C. T. W. & McGlaughlin, A. L. (1991) *Magn. Reson. Med.* 18, 80–92 ; and (iii) the use of anionic paramagnetic shift reagents (SRs) Bansal, N., Germann, M. J., Lazar, I., Malloy, C. R. & Sherry, A. D. (1992) *J. Magn. Reson. Imaging,* 2, 385–391. Each approach has disadvantages, especially for in vivo applications. It is now clear that the methods based on relaxation time differences and MQF's do not accurately filter intra- versus extracellular signals Hutchison, R. B., Malhotra, D., Hendrick, R. E., Chan, L. & Shapiro, J. L. (1990) *J. Biol. Chem* 265, 15506–15510. In addition, the time required for data collection with these techniques limits their utility Lee, H. J., Labadie, C. & Springer, C. S. (1992) *Abstr.* 11th Mtg. SMRM, 2214. The primary disadvantage of paramagnetic SRs concerns possible acute toxicity Boulanger, Y., Fleser, A., Amarouche, R., Ammann, H., Bergeron, M. & Vinay, P. (1992) *NMR Biomed.* 5, 1–10. Since most SRs for biological cations are by necessity anionic and bind competitively with all biological cations, they could unknowingly compromise the physiology of an organ by disrupting normal $Ca^{2+}$,$Mg^{2+}$,$Na^+$ or $K^+$ ion gradients. Despite this disadvantage, SRs do allow simultaneous measurement of $^{23}$Na signals from multiple tissue compartments so that relative changes in $Na^+$ ion concentrations can be detected in various compartments with excellent temporal resolution.

A number of different SRs have been successfully used to monitor intracellular sodium in isolated cells and perfused tissue Buster, D. C., Castro, M. M. C. A., Geraldes, C. F. G. C., Malloy, C. R., Sherry, A. D. & Siemers, T. C. (1990) *Magn. Reson. Med.* 15, 25–32 but only dysprosium(III) triethylenetetraminehexaacetate ($DyTTHA^{2-}$) Blum, H., Osbakken, M. D. & Johnson, R. G. (1991) *Magn. Reson. Med.* 18, 348–357 and thulium(III) 1,4,7,10-tetraazacyclododecane-1,4,7,10-tetrakis (methylene phosphonate) ($TmDOTP^{5-}$) Bansal, N., Germann, M. J., Lazar, I., Malloy, C. R. & Sherry, A. D. (1991) *J. Magn. Reson. Imaging,* 2, 385–391 have been used in vivo. Previously, $TmDOTP^{5-}$ aided $^{23}$Na chemical shift imaging has been used in combination with $^{23}$Na and $^1$H imaging to monitor $Na^+$ in successive 1 mm slices in the rat brain in vivo. Like various relaxation agents used in MRI, the shift reagent (SR) does not cross the blood brain barrier Bansal, N., Germann, M. J., Lazar, I., Malloy, C. R. & Sherry, A. D. (1992) *J. Magn. Reson. Imaging,* 2, 385–391.

Major trauma frequently leads to multiple organ failure and death. Trauma centers throughout the country deal with serious injury arising from multiple fractures, ischemic injury or burn victims. Initial treatment is concerned with immediate control of overt damage such as bleeding, but must also be concerned with the cascade effects which may manifest several hours or even days after the initial trauma.

Damage to any of the major organs is a grave concern; however determination of liver damage is of particular interest because malfunction of this organ is considered to be a bellwether of multisystem failure. Unfortunately, many of the conventional methods of determining liver function do not necessarily reflect function of the organ but may be the result of remote physiological or physical damage.

Liver function is conventionally determined by measuring prothrombin times, selected enzyme activities such as SGOT, SGOT or bilirubin or albumin levels. Such tests do however require a blood sample to be drawn and time to run the tests. And there appears to be no particular parameter that is related to predicting liver function, i.e. whether or not the liver has itself been irreversibly damaged or whether abnormal enzyme levels are merely a manifestation of skeletal damage.

SUMMARY OF THE INVENTION

The present invention addresses the foregoing and other problems by providing efficient, noninvasive methods of rapidly determining intracellular sodium ion levels in vivo employing nuclear magnetic resonance. This allows assessment of the extent of injury to major organs such as the heart and liver, as well as brain, kidney or muscle. Methods are disclosed for determining response of liver function to traumatic injury such as burns. The methods may also be applied to relate intracellular sodium increase to the extent of ischemia in heart tissue.

The method is based on the use of nuclear magnetic resonance for in vivo determinations. The method is practical for in vivo whole body measurements in humans and is attractive because noninvasive procedures may be employed. When desiring to measure intracellular sodium ion levels, one will first prepare a solution of the appropriate shift reagent, preferably TmDOTP$^{5-}$, in water. pH is preferably adjusted to physiological range, i.e., 7.2–7.4 using sodium or potassium hydroxide. There are of course several pharmacologically acceptable solutions that could be employed, meaning compositions that do not produce an allergic or similar untoward reaction when administered to a human.

Typically, the compositions will be administered in injectable form, suitably buffered if necessary. Usually the diluent will be made isotonic with sufficient saline or glucose. Such solutions are suitable for intravenous, intramuscular, subcutaneous and intraperitoneal administration. In this connection, sterile aqueous media which can be employed will be known to those of skill in the art; for example, one dosage could be dissolved in 1 mL of isotonic NaCl solution and either added to 1000 mL of hypodermoclysis fluid or injected at the proposed site of infusion (see for example, Remington's Pharmaceutical Sciences:, 15th Edition, pages 1035–1038 and 1570–1580). Some variation in dosage will necessarily occur depending on the condition of the subject. The person responsible for administration will, in any event, determine the appropriate dose for the individual subject.

Administration is preferably by infusion. Stock solutions are preferably on the order of 80 mM for TmDOTP$^-$ but other convenient concentrations may be used. Initial infusions should be relatively slow, for example rates of 2 ml per hr for 6 min may be employed for 0.45 kg mammals while 200–300 ml per hr for the same period of time would be employed for an average 70 kg human. It is preferable to decrease the infusion rate after the initial infusion so that chemical shift is maintained. Infusion should for a sufficient amount of time to allow the shift reagent to contact the tissue or organ in which one desires to measure the sodium or potassium ion concentration and to make the measurements. The correct amount of diffusion time will be apparent when measured chemical shift differences of about 3–7 ppm between intra- and extra-cellular sodium ion resonances are achieved.

The actual NMR measurement is conveniently made with a surface coil positioned on or near the tissue in which sodium or potassium ion resonances are measured. For small animals, typically this is a 2–3 cm diameter surface coil tuned to the appropriate frequency for $^{23}$Na, i.e., 53 MHz at 4.7 T. For $^{23}$Na, the inventors have employed a 50 $\mu$S excitation pulse followed by a 10 $\mu$s dead time and 1024 real data points collected over a sweep width of 3000 Hz. The coil itself may be placed on the skin of the subject, for example on the chest over the heart or liver. In cases where the tissue or organ is already exposed, as during a surgical procedure, the coil may be placed directly on the organ or tissue.

The method generally allows one to detect and differentiate sodium in the intracellular and extracellular compartments. This feature allows two types of measurements, both of which are important; first, since the resonances from each compartment are resolved, the relative amounts of NMR-visible sodium in both compartments are easily measured; second, $T_1$ (spin-lattice) and $T_2$ (spin-spin) relaxation times of sodium in each compartment can be measured in vivo. The relaxation times provide information about the physical state of the sodium ion. Once the intracellular and extracellular signals are resolved, measurements of $T_1$ and $T_2$ may be performed by a variety of well known methods. Similar methods may be applied to $^{39}$K.

An important aspect of the invention is that the shift reagent solution is a calcium-ion free solution. This is surprising as the inventors are the first to show that calcium ion does not have to be added to the shift reagent, as is generally required in isolated perfused heart experiments to maintain extracellular calcium ion levels. An additional observation was that the dose levels of TmDOTP$^{5-}$ employed to obtain baseline resolution of the sodium ion resonances were physiologically non-perturbing, even though the osmotic load was high.

The method is particularly useful for determining liver function subsequent to systemic injury. In animal cutaneous burn injury models for example, the inventors have demonstrated intracellular sodium ion levels following burn injury increase significantly, indicating liver injury in spite of normal levels of high energy phosphates. The intracellular sodium ion levels may be used as a guidepost for the severity of injury and as a bellwether for recovery. The disclosed nmr method is ideal for this purpose as it is noninvasive. For burn victims of major systemic injury it provides a new window on function of an organ that is critical to survival.

Analogously, the method is useful for detecting ischemic damage, as demonstrated with myocardial tissue. For example, it is well established that reduced blood supply to heart muscle can cause irreversible damage. However, the proper treatment for these patients (revascularization by surgery or angioplasty compared to supportive care) is often difficult to establish. Recently it has been shown that intracellular sodium accumulates quickly after myocardial ischemia and can be used as a direct index of reduced flow to heart muscle.

Similar methods and techniques apply to the determination of intra and extracellular potassium ion. Because the disclosed methods provide baseline-resolved spectra from in vivo measurements of intra and extracellular $^{23}$Na (or $^{39}$K), well-known methods employing frequency shift selective imaging techniques can provide images of sodium or potassium ions in each compartment.

BRIEF DESCRIPTION OF THE DRAWINGS

FIG. 5A is a $^{23}$Na magnetic resonance spectra of rat liver in vivo obtained before and after infusion of thulium (III) 1,4,7,10-tetraazacyclodedecane N,N',N'',N'''-tetra (methylenephosphonate). The extracellular Na$^+$ signal (E)

Figure 1A:
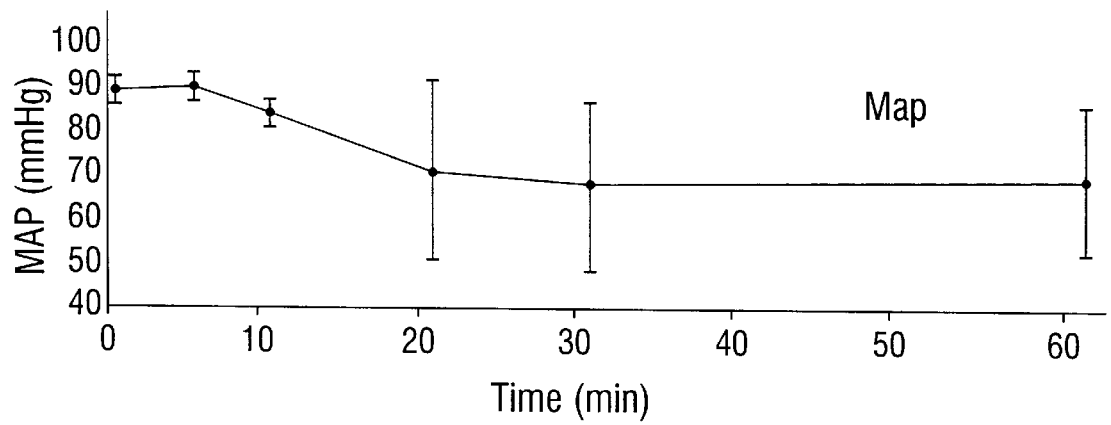
FIG. 1A, FIG. 1B, FIG. 1C and FIG. 1D show plots of mean arterial pressure (MAP), resting liver transmembrane potential (-$E_m$) and free $Ca^{2+}$ levels in serum during infusion of 80 mM TmDOTP$^{5-}$ at the rates indicated in the lower panel. The error bars represent ± one standard deviation (n=7).
Figure 1B:
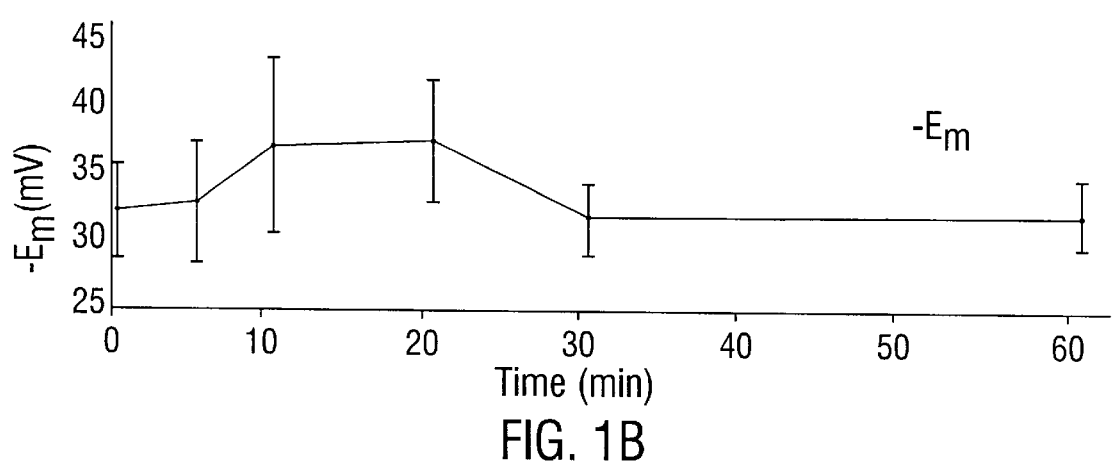
Figure 1C:
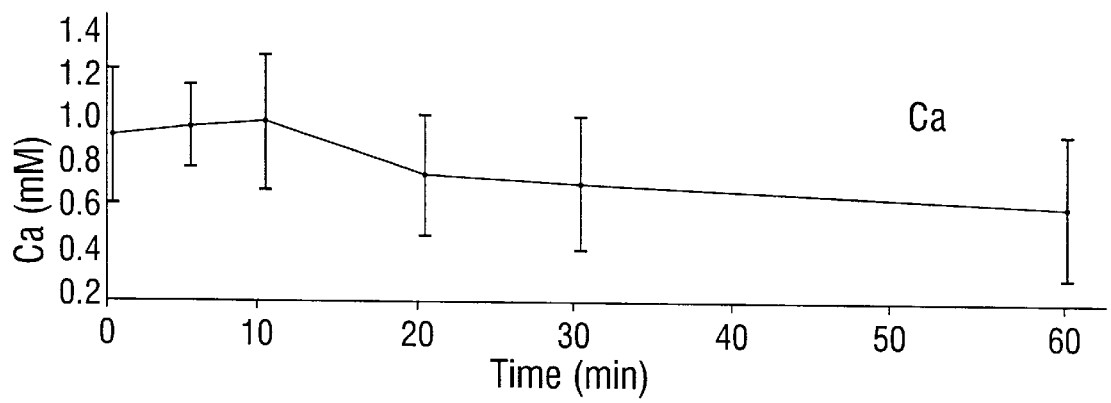
Figure 1D:
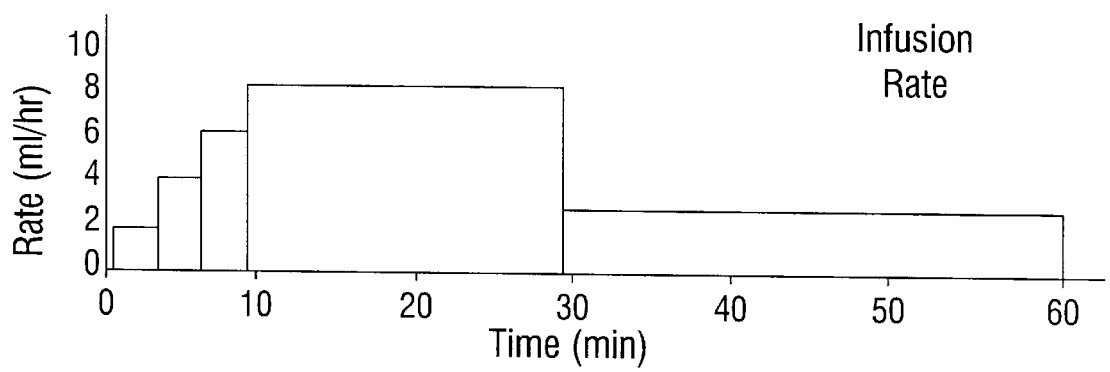

was shifted away from the intracellular Na$^+$ signal (I). The spectrum is from a sham burn control animal.

Figure 5B shows a $^{23}$Na magnetic resonance spectrum of a burned rat under the same experimental conditions as in FIG. 5A.

FIGS. 6A and FIG. 6B show matched $^{31}$P magnetic resonance spectra and $^{23}$Na spectra of typical in vivo rat liver from sham burn control groups. Peak assignments in the $^{31}$P spectrum are: P$_m$, phosphomonoesters; P$_d$, phosphodiesters.

FIGS. 6C and FIG. 6D show analogous matched $^{23}$Na and $^{31}$P magnetic resonance spectra as in FIGS. 6A and 6B for burn groups.

DETAILED DESCRIPTION OF PREFERRED EMBODIMENTS

Shift Reagents: 80 mM stock solutions of TmDOTP$^{5-}$ were prepared as described in Bansal, N., Germann, M. J., Lazar, I., Malloy, C. R. & Sherry, A. D. (1992) *J. Magn. Reson. Imaging*, 2, 385–391. DyTTHA$^{3-}$ was prepared by mixing DyCl$_3$ with a slight molar excess of TTHA (Sigma Chemical Co., St. Louis, Mo.) in water and titrating with NaOH to a pH of 7.4. The final concentration of DyTTHA$^{3-}$ was 400 mM.

Animal Preparation: Male Sprague-Dawley rats weighing 350–450 g were initially anesthetized by intramuscular injection of a 0.5 ml mixture of ketamine (13 mg/ml) and xylazine (87 mg/ml). Both jugular veins and a carotid artery were cannulated through a midline neck incision. One jugular vein was used to maintain the anesthesia (2 mg/ml ketamine, 0.25 mg/ml xylazine in 5% guaifenesin) at a rate of 2–3 ml/hour, and the other was used to infuse SR. The blood pressure and heart rate were continuously monitored from the carotid artery during the NMR experiments using a Gould transducer and Coulbourn polygraph. A tracheotomy was performed and the rat was connected to a respirator and maintained at a respiration rate of 90 breaths/minute and a tidal volume of 3 cc. The rats were also nephrectomized to eliminate clearance of the shift reagent, except in those animals where SR clearance was measured. Livers were exposed through a subcostal incision and a surface coil was positioned directly on the liver with the animal in a supine position. The animals were maintained at 37° C. using a water recirculating heating pad.

SR Infusion: Stock solutions of 80 mM TmDOTP$^{5-}$ or 400 mM DyTTHA$^{3-}$ were initially infused at a rate of 2 ml/hr for 6 minutes. The rate was slowly increased to 8 ml/hr over 6 min, then maintained at this level for 20 to 30 minutes. After achieving a chemical shift difference of 5–7 ppm between the intra- and extracellular sodium resonances, the infusion rate was reduced to 2–3 ml/hr. No Ca$^{2+}$ was added during infusion of either SR.

NMR Data Collection: All in vivo NMR experiments were performed on a 4.7-T 40-cm GE CSI Omega spectrometer (GE NMR Instruments, Fremont, Calif.). Shimming was performed on the sodium signal. A sodium line width of 35–40 Hz was typical. Both $^{23}$Na and $^{31}$P spectra were collected in an interleaved fashion during TmDOTP$^{5-}$ infusion. A 2.3 cm diameter surface coil dual tuned to 53 MHz for $^{23}$Na and 81 MHz for $^{31}$P, using a circuit design as described in Schnall, M. D., Subramanian, V. H. & Leight, J. S. (1986) *J. Magn. Reson.* 67, 129–134. The coil performance was optimized such that there was less sensitivity loss at the $^{31}$P frequency as compared to at the $^{23}$Na frequency. For $^{23}$Na, a 50 μS excitation pulse was followed by a 10 μs dead time and 1024 real data points were collected over a sweep-width of 3000 Hz with the pre-amplifier filter turned off.

For $^{31}$P, a 30 μs pulse was followed by a 100 μs dead time and 2048 real data points were collected over a sweep-width of 5000 Hz with the pre-amplifier filter on. Switching of these parameters and the spectrometer frequency was executed by a script in an automated fashion. To take advantage of the short spin-lattice relaxation time of sodium, two $^{23}$Na acquisitions were collected between each $^{31}$P acquisition. Cyclops phase cycling was used for both the nuclei. The minimum repetition time for $^{23}$Na was 0.34 s and for $^{31}$P was 3.66 s. The data were initially collected as a sum of 64 acquisitions for $^{23}$Na and 32 acquisitions for $^{31}$P over 1.95 minute intervals. For the data presented in FIG. 1, four consecutive $^{31}$P FIDs were summed resulting in 128 acquisitions per spectrum collected over a 7.8 minute period. The FIDs were Fourier transformed after base-line correction and a single exponential multiplication corresponding to 10 Hz line broadening for $^{23}$Na and a 20 Hz line broadening for $^{31}$P.

$^{23}$Na spin-lattice (T$_1$) and spin-spin (T$_2$) relaxation times were measured before and after TmDOTP$^{5-}$ infusion using a 2 cm surface coil single tuned to 53 MHz. The instrument dead-time was set to 10 μs for all relaxation experiments. A pulse-burst saturation recovery experiment was performed using 50 saturation pulses (23 μs) followed by an incremental delay (15 values ranging from 1 ms to 256 ms) and 23 μs excitation pulse. Cyclops phase-cycling was used for measurement of T$_1$. A Hahn spin-echo experiment with exorcycle phase-cycling was used for measurement of T$_2$. A 23 μs excitation pulse and a 46 μs refocusing pulse was used and the spin echo time was varied from 0.05 ms to 40 ms in 25 steps. The instrument dead-time of 10 μs was included as a part of the echo time. 1024 real data points were collected over a sweep width of 3000 Hz and either 128 or 256 transients were acquired at each delay for both T$_1$ and T$_2$ experiments. Each T$_1$ was measured five times on three rats (two animals were studied twice) and each T$_2$ was measured nine times on five rats (four animals were studied twice).

The relaxation times were computed by fitting the peak integral of the resonances to both mono- and bi-exponential functions. Measurement of T$_2$ with a surface coil was validated by comparing the T$_2$ values of a normal saline solution determined using a volume coil versus a surface coil. The T$_2$ values obtained by the two coils were identical. The relaxation times of extracellular Na$^+$ in the absence of TmDOTP$^{5-}$ were calculated by subtracting the raw relaxation curves of intracellular Na$^+$ from the corresponding raw relaxation curves of total Na$^+$ without SR. The subtracted curves were then fit to mono- and bi-exponential functions. These calculations assume that the presence of TmDOTP$^{5-}$ in extracellular spaces does not change the relaxation time of intracellular Na$^+$. The fact that no change in the intracellular $^{23}$Na line-width during infusion of increasing quantities of TmDOTP$^{5-}$ was observed suggested this assumption should be valid. Also, Burstein, D. & Fossel E. T. (1987) *Magn. Reson. Med.* 4, 261–273 have shown that doubling the concentration of Dy(PPP)$_2$$^{7-}$ did not change the relaxation times of intracellular Na$^+$ in perfused frog hearts.

The use of TmDOTP$^{5-}$ as an in vivo $^{23}$Na NMR shift reagent for rat liver was evaluated by collecting interleaved $^{23}$Na and $^{31}$P spectra. Infusion of 80 mM TmDOTP$^{5-}$ without added Ca$^{2+}$ produced baseline resolved peaks from intra- and extracellular sodium without producing any changes in phosphate metabolite resonances or intracellular pH. Several key physiological parameters measured in parallel groups of animals confirmed that liver physiology is largely unaffected by this shift reagent. A direct comparison of TmDOTP$^{5-}$ versus DyTTHA$^{3-}$ showed that after infusing 5 to 8 times more DyTTHA$^{3-}$, the extracellular sodium peak shifted by the same amount as with TmDOTP$^{5-}$, but the two $^{23}$Na resonances were very broad and not resolved. The baseline resolved peaks with TmDOTP$^{5-}$ allowed measurement of the in vivo $T_1$ and $T_2$ relaxation characteristics of intra- and extracellular Na$^+$. The measured $T_1$, $T_{2s}$ and $T_{2f}$ values and the relative contributions from the slow and fast $T_2$ components for intracellular Na$^+$ in liver did not differ significantly from the values reported for perfused frog heart. The $T_1$ and $T_2$ relaxation curves of the extracellular Na$^+$ resonances fit a mono-exponential function. Analysis of the relative contribution of the fast and slow relaxing $T_2$ components from intracellular Na$^+$ resulted in a calculated visibility factor of 69±4% and the intracellular Na$^+$ concentration calculated from the NMR peak intensity ratio, the measured visibility factor and literature values of intra- and extracellular volume was 16 mM. These results indicate that TmDOTP$^{5-}$ is useful as an in vivo shift reagent for liver and other organs.

EXAMPLE 1

The following experiments were performed by the inventors and show for the first time that in vivo measurements using the TmDOTP$^{5-}$ shift reagent will provide quantitative measurements of intra- and extracellular sodium ion.

Physiological Measurements

Several key physiological measurements were obtained on a group of animals (n=7) during infusion of TmDOTP$^{5-}$ using the same protocol as used during all subsequent NMR measurements. No significant changes in heart rate (240±20) or developed pressure (40±5 mm Hg) were observed but the mean arterial pressure (MAP) tended to decrease from about 90 mm Hg to 70 mm Hg during infusion of the SR (see FIG. 1A, FIG. 1B, FIG. 1C and FIG. 1D). The decrease in MAP appeared to parallel a relatively small change in free Ca$^{2+}$ levels in blood serum as detected by a calcium specific electrode. Excess Ca$^{2+}$ was not coadded with the SR in these experiments, unlike in isolated perfused heart experiments where excess Ca$^{2+}$ must be coadded with TmDOTP$^{5-}$ to maintain an extracellular free [Ca$^{2+}$] of about 1 mM. It has been previously shown that Ca$^{2+}$ is rapidly released from body stores during infusion of TmDOTP$^{5-}$ into live rats Bansal, N., Germann, M. J., Lazar, I., Malloy, C. R. & Sherry, A. D. (1992) *J. Magn. Reson. Imaging,* 2, 385–391.

The resting transmembrane potential ($-E_m$) was measured in in vivo exposed livers using a modified Ling-Gerard ultramicroelectrode Holliday, R. L., Illner, H. P. & Shires, G. T. (1981) *J. Surg. Res.* 31, 506–515. Serum sodium, potassium, and hemoglobin concentrations as well as arterial pH, pCO$_2$ and pO$_2$ were monitored throughout the infusion protocol using a standard clinical blood gas analyzer. The resting transmembrane potential tended to increase during the highest infusion rates (FIG. 1A, FIG. 1B, FIG. 1C and FIG. 1D) then return to basal levels during lower levels of steady-state infusion of the SR. Serum sodium increased by only 10 meq/L during the entire infusion protocol (from 149±3 to 158±5 meq/L) even though the total amount of sodium infused with the SR was substantial. Serum potassium (3.5±0.2 meq/L), hemoglobin (13±1 g/dL), pH (7.36±0.02), pCO$_2$ (45±2 mm Hg) and pO$_2$ (120±8 mm Hg) remained unchanged throughout the protocol. These results suggest that basic liver physiology is largely unaffected by TmDOTP$^{5-}$ at the doses required for baseline resolution of the intra- and extracellular $^{23}$Na resonances.

$^{23}$Na Shift Experiments

Figure 2A:
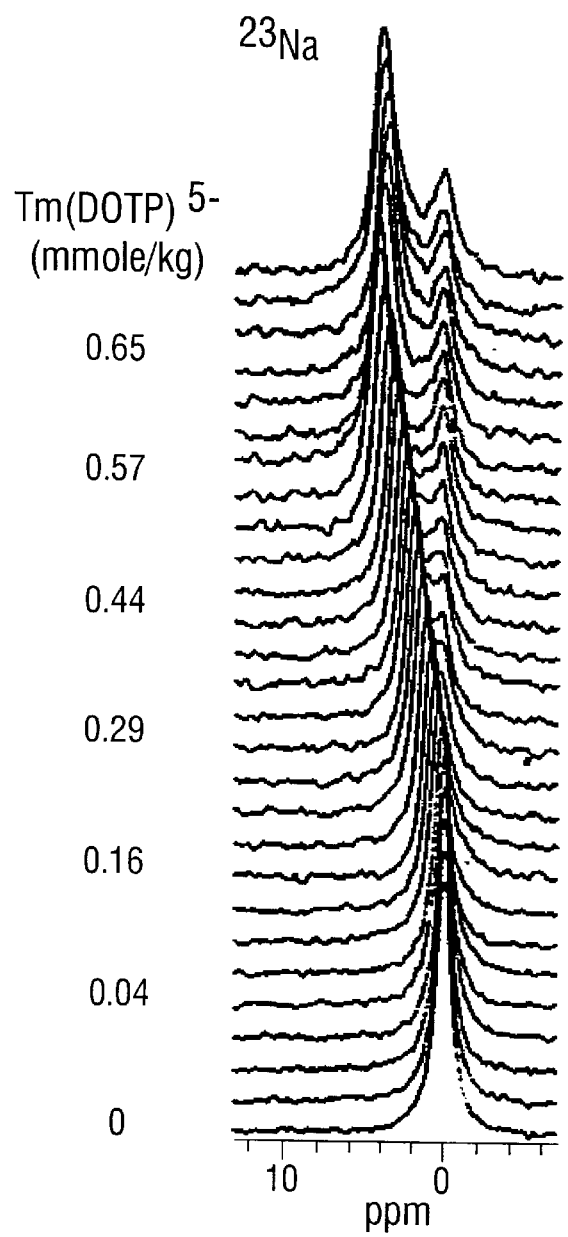
FIG. 2A and FIG. 2B show stacked plots of interleaved $^{23}$Na (left) and $^{31}$P (right) spectra from rat liver in vivo collected during TmDOTP$^{5-}$ infusion. The time indicated at the right of each $^{31}$P spectrum is at the beginning of data acquisition. The infusion doses at the corresponding time intervals are shown at the left of $^{23}$Na spectra.
Figure 2B:
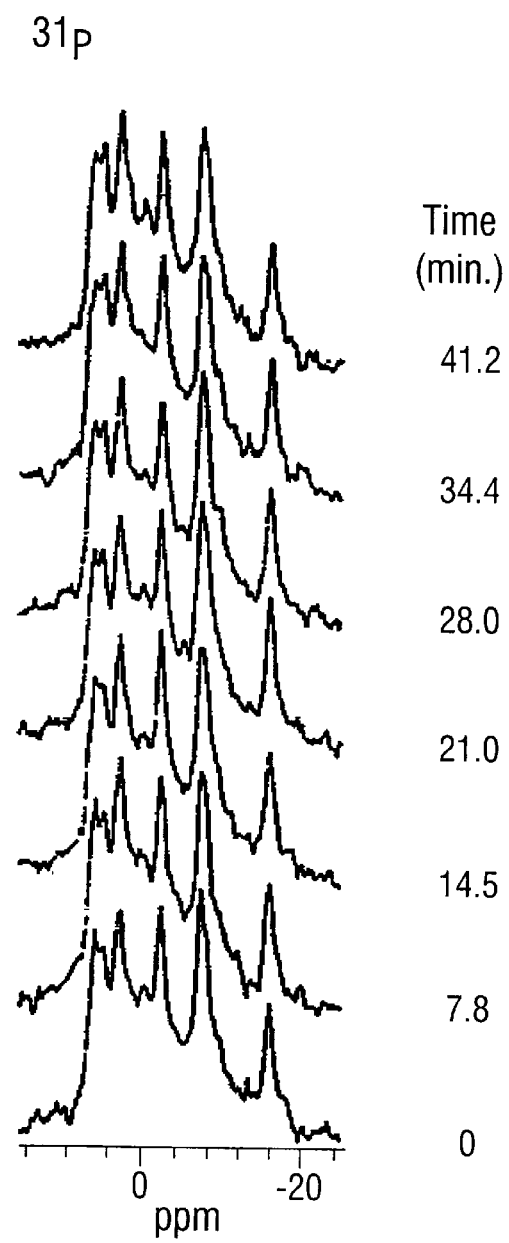

Interleaved $^{23}$Na and $^{31}$P spectra collected during TmDOTP$^{5-}$ infusion are shown in FIG. 2A and FIG. 2B. In contrast to a $^{23}$Na brain study Bansal, N., Germann, M. J., Lazar, I., Malloy, C. R. & Sherry, A. D. (1992) *J. Magn. Reson. Imaging,* 2, 385–391 where two shifted resonances appeared early during the infusion (assigned to vascular and interstitial Na$^+$), the paramagnetically shifted $^{23}$Na resonance in the in vivo liver remained a single symmetrical resonance throughout the infusion period. The intra- and extracellular $^{23}$Na resonances were clearly resolved after 0.55 mmole kg$^{-1}$ (body weight) of TmDOTP$^{5-}$ had been introduced. After a 0.65 mmoles kg$^{-1}$ dose of SR, the extracellular Na$^+$ was paramagnetically shifted by approximately 5 ppm. Once discernible from the extracellular Na$^+$ peak, the intracellular Na$^+$ peak intensity did not change with further infusion of SR suggesting that TmDOTP$^{5-}$ does not alter the intracellular Na$^+$ concentration in the liver at these dosages.

The $^{31}$P spectra collected before and during the TmDOTP$^{5-}$ infusion showed three ATP resonances, a single inorganic phosphate resonance and one sugar phosphate resonance. The intensity of the phosphocreatine resonance was quite low indicating that the spectra were mainly from the liver and did not have any significant contributions from the surrounding tissue. The $^{31}$P spectra also showed an underlying broad signal. This broad signal has been reported by other investigators Bates, T. E., Williams, S. R. & Gadian D. G. (1989) *Magn. Reson. Med.* 12, 145–150 and has been assigned to phosphodiesters in the phospholipid bilayer. The $^{31}$P resonance areas and chemical shifts were unaffected by the SR indicating that TmDOTP$^{5-}$ does not alter the cellular energy state of the liver. The intracellular pH calculated from the shift of inorganic phosphate peak was also unaffected by the SR. The $^{23}$Na and $^{31}$P spectra shown in FIG. 2A and 2B were collected using the double tuned 2.3 cm surface coil described in methods. $^{23}$Na spectra were also collected using a 1 cm surface coil and these showed a very similar ratio of intra- and extracellular Na$^+$. This indicated that the 2.3 cm coil sampled only liver tissue and not some average of liver, muscle and/or intestine.

Figure 3A:
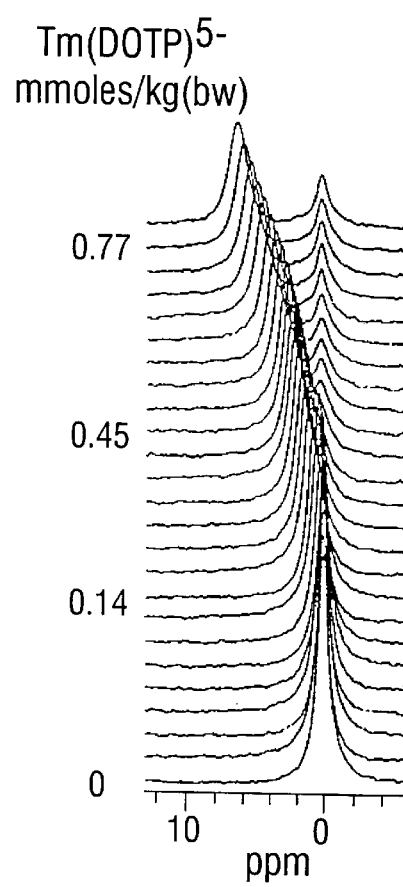
FIG. 3A and FIG. 3B show a comparison of $^{23}$Na spectra from rat liver during TmDOTP$^{5-}$ (left) and DyTTHA$^{3-}$ (right) infusion. The time indicated in the middle of the stacked plots is at the beginning of data acquisition. The infusion doses at the corresponding time intervals are shown at the left for TmDOTP$^{5-}$ and at the right for DyTTHA$^3$.
Figure 3B:
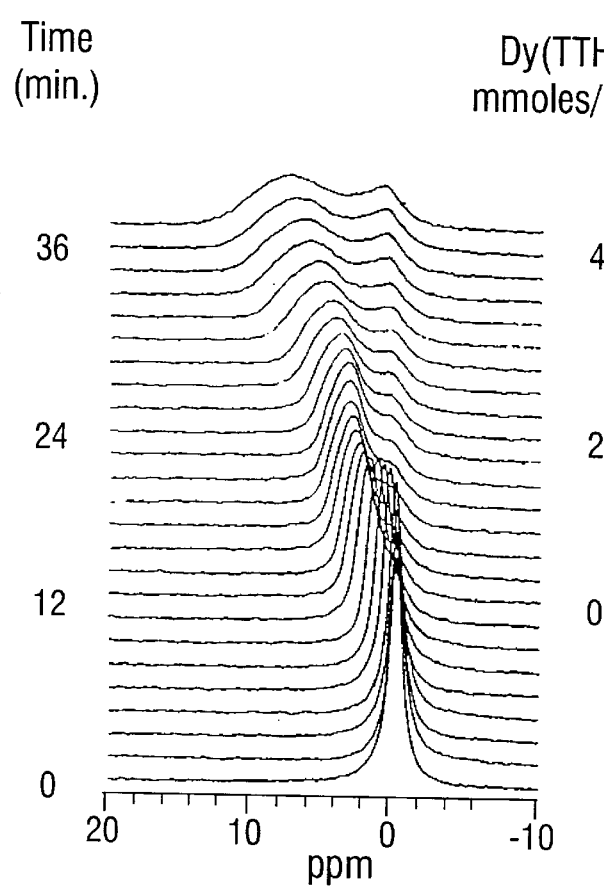

A direct comparison of TmDOTP$^{5-}$ versus DyTTHA$^{3-}$ as a $^{23}$Na shift reagent in the in vivo liver is shown in FIG. 3A and FIG. 3B. Although the animals remained hemodynamically more stable during infusion of DyTTHA$^{3-}$, this SR induced a much lower $^{23}$Na shift per unit concentration and more severe line broadening than did TmDOTP$^{5-}$. The dose of DyTTHA$^{3-}$ required to induce a shift of 5 ppm was 3.74 mmoles kg$^{-1}$ body weight as compared to 0.65 mmoles kg$^{-1}$ of TmDOTP$^{5-}$. Also, the peak width at half height for the intra- and extracellular resonances when separated by 5 ppm were 195 and 300 Hz, respectively, for DyTTHA$^{3-}$ but only 70 and 80 Hz for TmDOTP$^{5-}$. The greater line-widths produced by DyTTHA$^{3-}$ result from a combination of larger bulk magnetic susceptibility of Dy(III) versus Tm(III) and the higher concentration of DyTTHA$^{3-}$ required to separate the intra- and extracellular resonances.

The fact that the line-width of the intracellular resonance was broadened by nearly a factor of 3 for DyTTHA$^{3-}$ versus TmDOTP$^{5-}$ indicated that bulk susceptibility broadening is particularly severe with the Dy(III) reagent. Infusion of higher doses of DyTTHA$^{3-}$ did not improve the resolution of intra- and extracellular resonances because higher doses increased the line-widths even further.

The washout rate of TmDOTP$^{5-}$ was measured by monitoring the frequency of the shifted $^{23}$Na peak after stopping the infusion. The chemical shift versus time data fit to an exponential decay function yielded at $t_{1/2}$ of 9 minutes (n=2). This half life is shorter than the $t_{1/2}$ of 37 minutes for washout of TmDOTP$^{5-}$ from rat brain and a $t_{1/2}$ of 44 minutes for washout of DyTTHA$^{3-}$ from rat muscle. A recent CSI study indicated that most of the shifted $^{23}$Na signal detected by a surface coil in a rat brain experiment actually arises from Na$^+$ in muscle surrounding the skull and hence the agreement between the muscle and brain studies would be expected. The significantly shorter $t_{1/2}$ measured for washout of TmDOTP$^{5-}$ from the liver interstitium likely reflects greater blood flow in liver relative to resting muscle.

$T_1$ and $T_2$ Relaxation Measurements

All relaxation measurements were obtained on animals where the intra- and extracellular $^{23}$Na resonances were baseline resolved (such as that shown in FIG. 3A and FIG. 3B). The results of those measurements are summarized in Table I. The relaxation times of extracellular Na$^+$ in the absence of TmDOTP$^{5-}$ were calculated by the subtraction method described in the experimental section. Theory predicts that both $T_1$ and $T_2$ for a spin 3/2 nuclei such as $^{23}$Na are bi-exponential in tissues where the correlation time is not short compared to the Larmor period; the theoretical ratio of fast to slow relaxing components is 20:80 for $T_1$ relaxation and 60:40 for $T_2$ relaxation Hubbard, P. S. (1970) *J. Chem. Phys.* 53, 985–987. However, all of the experimental $T_1$ relaxation curves and extracellular $T_2$ relaxation curves (without SR) fit a single exponential function rather well. The two $T_1$ relaxation components may not be separable because their values may differ by less than an order of magnitude or because the fast component accounts for only 20% of the total signal intensity and is therefore more difficult to detect experimentally.

fast and slow components are indeed present. It is possible that the time constants for the two components do not differ significantly. Shinar & Navon (1986) have shown that a single exponential would be observed if $T_{2s}/T_{2f} \leq 2$ or that the short $T_2$ component is not detected because of particular exchange conditions between the vascular and interstitial spaces. The relative contribution of the two $T_2$ relaxation components of the combined intra- and extracellular resonance was 16:84 (fast:slow) before SR infusion and 42:58 for the resolved intracellular resonance after SR infusion. The apparent decrease in fast component contribution for the combined resonance before SR infusion as compared to the intracellular resonant is consistent with mono-exponential $T_2$ decay (slow component only) of extracellular Na$^+$ in the absence of shift reagent.

The values of $T_1$, $T_{2f}$ and $T_{2s}$ found here for intracellular Na$^+$ in liver are nearly identical to the respective relaxation times reported for intracellular Na$^+$ in perfused frog hearts Foy, D. F. & Burstein D. (1990) *Biophys. J.* 58, 127–134. Interestingly, the relative contributions from the fast and slow $T_2$ components for intracellular Na$^+$ were also nearly the same in the two tissues (42:58 in liver versus 48:52 in frog hearts) and neither agrees with the theoretically expected 60:40 ratio for a single pool of intracellular Na$^+$ experiencing bi-exponential relaxation due to quadripolar effects. This discrepancy could arise from several slightly different pools of sodium with a distribution of fast and slow relaxation times each contributing to the intracellular resonance, where some of the fast relaxing components decay so rapidly that their detection is partly or completely missed even with echo times as short as 50 μs. Assuming that

TABLE I

Experimental $^{23}$Na Relaxation Times and % Fast and Slow $T_2$ Components in Rat Liver.

| | Shift Reagent | $T_1$ | % $T_{2(slow)}$ | $T_{2(slow)}$ | % $T_{2(fast)}$ | $T_{2(fast)}$ |
|---|---|---|---|---|---|---|
| Absent | Combined intra- and extracellular | 33.8 ± 0.3 | 84 ± 3 | 17.3 ± 0.8 | 16 ± 3 | 1.8 ± 0.3 |
| Present | Shifted Peak, | 23.9 ± 1.0 | 100 | 10.0 ± 2.8 | | |
| | Intracellular | 21.1 ± 0.6 | 58 ± 3 | 13.0 ± 0.9 | 42 ± 3 | 1.3 ± 0.1 |
| Absent | Extracellular (Calculated) | 41.0 ± 1.0 | 100 | 18.0 ± 0.8 | | |

Figure 4:
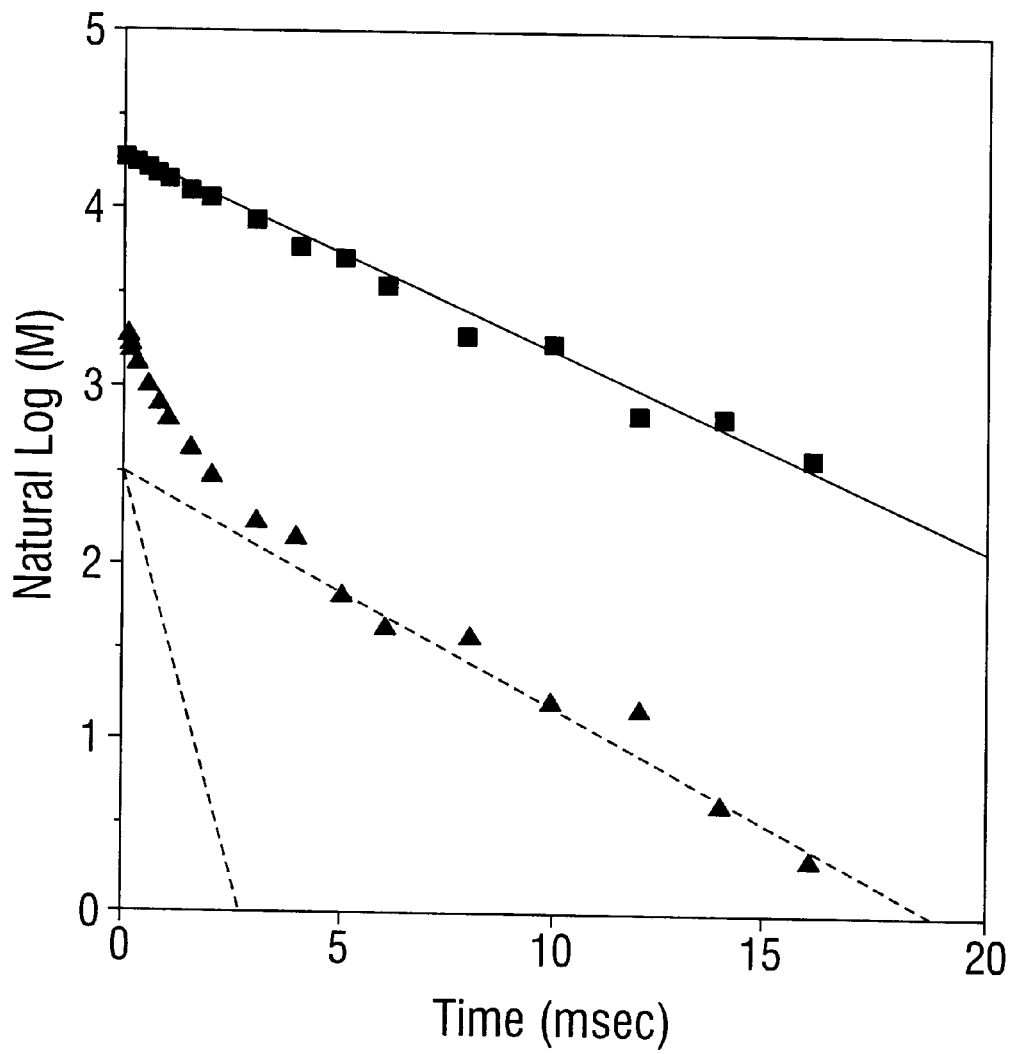
FIG. 4 represents a semilogarithmic plot of $T_2$ relaxation curve for intracellular (▲) and purely extracellular (■) sodium. The purely extracellular sodium curve was calculated by the subtraction method described in the text.

FIG. 4 compares the semilogarthmic plots of $T_2$ decay for intracellular and purely extracellular Na$^+$ (calculated by subtraction). The intracellular plot shows a two component curve while the purely extracellular Na$^+$ plot shows a straight line indicating a single component decay. The observed mono-exponential $T_2$ decay for extracellular sodium in rat liver in vivo agrees with the observed single exponential $T_2$ decay in human serum Shinar, H. and Navon, G. (1986) *Magn. Res. Med.* 3, 927–934 and contrasts with the reported bi-exponential $T_2$ decay of interstitial sodium in perfused frog and rat hearts Foy, D. F. & Burstein D. (1990) *Biophys. J.* 58, 127–134. The shifted extracellular liver $^{23}$Na resonance clearly has significant contributions from both serum sodium and interstitial sodium. Our observation of a single, symmetrical extracellular sodium resonance both during infusion of TmDOTP$^{5-}$ and during washout of the agent indicates that Na$^+$ ion exchange between the vascular and interstitial space in liver is quite rapid. The measured $T_1$ and $T_2$ values for this resonance likely represent an average of the relaxation rates of sodium in the two compartments.

Failure to detect two $T_2$ components in the extracellular $^{23}$Na resonance does not exclude the possibility that both the slow relaxing component is 100% visible but some of the rapidly decaying components are not visible (for either chemical or instrumental reasons), then the experimental fast:slow ratio of 42:58 or (29:40 after normalizing the slow component to 40%) implies that the visibility of total intracellular sodium is 29+40=69±4% (n=9).

Blum, H. Oskakkken, M. D. & Johnson, R. G. (1991) *Magn. Reson Med.* 18, 348–357, have also reported that intracellular Na$^+$ in liver is 53±21% visible. One should note however that there may be considerable error in the estimated 69% visibility because different pools of sodium ions may be exchanging with each other with different time constants and this could significantly affect the $T_{2f}$ relaxation contribution. However, the observed ratio of 29:40 for the fast:slow components, respectively, clearly suggests that there is a substantial amount of intracellular sodium in liver that is invisible with a 50 μs spin-echo time, or in a one pulse experiment with a dead time of 10 μs. This is in contrast with the near 100% visibility found for intracellular sodium in Na$^+$-load yeast cells Rooney, W. D. & springer, C. S. (1991) *NMR Biomed.*, 4, 227–245, using spectrometer dead times of less than about 25 μs.

This study demonstrates that TmDOTP$^{5-}$ can produce baseline resolved intra- and extracellular $^{23}$Na resonances in the in vivo rat liver at relatively low doses of SR. The physiological measurements reported here indicate that this amount of SR is unexpectedly quite non-perturbing to the animal, even though the osmotic load is high. This dose is about 4–6 times greater than a typical dose of MRI contrast agent (0.1–0.2 mmole kg$^{-1}$), such as GdDTPA$^{2-}$. The inventors are aware of only one other $^{23}$Na NMR study of in vivo liver using a SR. Blum, H., Osbakken, M. D. & Johnson, R. G. (1991) *Magn. Reson. Med.* 18, 348–357 infused 6 mmoles kg$^{-1}$h$^{-1}$ of DyTTHA$^{3-}$ for 60 to 90 minutes to discriminate between intra- and extracellular sodium. This SR dose is 8–12 times larger than the amount of TmDOTP$^{5-}$ employed using the methods of the present invention. After DyTTHA$^{3-}$ infusion, Blum, H., Osbakken, M. D. & Johnson, R. G. (1991) *Magn. Reson. Med.* 18, 348–357 reported that the extracellular Na$^+$ signal shifted downfield by about the same amount as in the present study, but the sodium resonances were very broad and were not resolved. This demonstrates that of the SR's reported so far, only TmDOTP$^{5-}$ can produce a baseline separation of intra- and extracellular $^{23}$Na resonances in liver. This is extremely important for valid measurement of tissues volumes, relaxation rates, and $^{23}$Na visibility during physiological interventions. TmDOTP$^{5-}$ also allows interleaved acquisition of $^{23}$Na and $^{31}$P NMR spectra without producing significant line broadening in the $^{31}$P spectrum.

Integration of the two resolved $^{23}$Na resonances gave a relative area ratio of 72:28 (extracellular:intracellular). A wide range of values has been reported for intra- and extracellular volume ratios and Na$^+$ concentrations in liver. If one assumes that the $V_{int}/V_{ext}$ volume ratio of 4.6 is reasonably representative of liver, then the observed peak area ratio of 72:28 gives the Na$_{int}$/Na$_{ext}$ concentration ratio of 0.12±0.04 after correction for 69% visibility of the intracellular signal. The measured extracellular Na$^+$ was 140 mM and therefore the intracellular concentration of Na$^+$ in liver as detected by NMR is ~16±5 mM. This value agrees with previously reported values measured using a variety of techniques Holliday, R. L., Illner, H. P. & Shires, G. T. (1981) *J. Surg. Res.* 31, 506–515 and Blum, H., Osbakken, M. D. & Johnson, R. G. (1991) *Magn. Reson. Med.* 18, 348–357.

As reported in Table I, the $T_1$'s for intra- and extracellular sodium calculated by subtraction are 21.1±0.6 and 41±1 ms, respectively. In contrast to the large differences in $T_1$ relaxation times of $^{31}$P metabolites in liver versus heart, the measured $^{23}$Na $T_1$ values in liver do not differ significantly from the $T_1$ values in perfused heart. It has been suggested that hepatic $^{31}$P $T_1$'s are much shorter due a higher concentration of paramagnetic ions in liver so, if this is true, the results presented here indicate that the $^{23}$Na $T_1$'s in liver are unaffected by these same paramagnetic ions.

The results indicate that TmDOTP$^{5-}$ may be safely used in intact animal studies without the co-addition of Ca$^{2+}$. TmDOTP$^{5-}$ induces a larger $^{23}$Na chemical shift per unit concentration due to a combination of larger negative charge as compared to DyTTHA$^{3-}$ and a more favorable Na$^+$ binding site geometry. Furthermore, both the shifted and unshifted signals are sharp and well resolved with TmDOTP$^{5-}$ because of smaller magnetic susceptibility of Tm(III) as compared to Dy(III). TmDOTP$^{5-}$ is useful for in vivo $^{23}$Na NMR studies of liver and other organs.

The present study has evaluated the use of TmDOTP$^{5-}$ in discriminating between different sodium compartments in the liver in live animals. For the first time, the in vivo relaxation characteristics of intra- and extracellular sodium and the relationship to tissue injury have been determined.

EXAMPLE 2

As mentioned, burn models are generally accepted as a model of major systemic injury and the consequences of that injury for hepatic metabolism. In such models, generally studied with rat models, burn injury has a correlation with liver damage and the ultimate survival of the animal. In this example, the inventors have shown that noninvasive measurement of a single parameter, i.e., intracellular and intracellular sodium ion concentration in the liver, can be used to indicate liver dysfunction and predicted survival. This method is rapid and noninvasive.

Rats with third degree burns covering 40% of the body surface were employed. Adult male Sprague-Dawley rats (300–500 g) were randomly divided into burn (n=7) and sham-burn (n=4) groups. Burn was inflicted by a standard model, as described in Kaufman, T. M. and J. W. Horton, (1992) *Am. J. Physiol.* 262 (*Heart Circ. Physiol.* 31) H1585–H1591. Rats were deeply anesthetized with methoxyflurane, shaved, and secured in a template device. A full-thickness scald burn over 40% of the total body surface area was produced by immersing the exposed body surface into a 100° C. water bath for 12 s on the back and sides. The animals were quickly dried after each exposure to avoid additional injury. No postburn analgesics were administered for this model, since the burn injury was a full-thickness burn that destroys all cutaneous nerve endings; as a result, the rats experienced no postburn pain as evidenced by their eating, drinking, moving freely around the cage, and responding to external stimulus. The sham-burn rats were anesthetized and handled in an identical manner except they were exposed to room temperature water. After recovery from inhalation anesthesia, the animals were placed in separate cages and given food and water ad libitum.

At 24-hr postburn, the animals were anesthetized by intramuscular injection of a 0.5 ml mixture of ketamine (87 mg/ml) and xylazine (13 mg/ml) and were placed on a warming blanket. The left femoral vein, left femoral artery, and left jugular vein were cannulated for supplemental anesthesia for arterial blood pressure measurement and for infusion of the shift reagent, respectively. Heparinized saline, 9 U/ml, was used in the arterial line. A midline laparotomy was performed to expose the liver, and the xiphoid process was removed. Each rat was then secured in a cradle in an upright position for the MRS experiments. A 2.2 cm diameter surface coil dual tuned to 47 MHz for $^{23}$Na and 72 MHz for $^{31}$P was positioned over the intersection of the three major lobes and the abdominal incision was sutured in separate layers around the insulated coil leads to prevent fluid and heat loss during NMR data collection.

Concurrent $^{23}$Na and $^{31}$P spectra were collected using a Nicolet NT 180 spectrometer with an Oxford 4.2 T vertical bore (130 mm) superconducting magnet. The field homogeneity was adjusted first with the $^1$H free induction decay (FID) from the liver and then with the $^{23}$Na FID for maximum field uniformity. A $^{23}$Na line width of 40–50 Hz was typical. $^{23}$Na spectra were generated from the summed FIDs of 100 excitation pulses (40 μs) at 105-ms intervals using 1,024 word data files and a sweep width of ±3000 Hz. The spectra were zero-filled to 4,096 points before Fourier transformation. The relative areas of the Na$^+$ (i) and Na$^+$ (e) resonances in the $^{23}$Na spectra and of the β-ATP and P$_i$ resonances in the phosphorus spectra were determined with the GEMCAP curve analysis program supplied with the Nicolet software.

Stock solutions of TmDOTP$^{5+}$ (80 mM) were prepared as described previously. After initial baseline spectra were obtained, infusion of TmDOTP$^5$ was begun at 0.5 mmol kg$^{-1}$ h$^{-1}$, and the rate was increased slowly to 1.2 or 1.6 mmol kg$^{-1}$ h$^-$ over a period of 12 min. After the Na$_e^+$ resonance shifted downfield by ~4 ppm, the infusion rate was reduced to ~0.6 mmol kg$^{-1}$ h$^{-1}$ and was maintained at this rate.

At the end of each experiment, a blood sample was collected from the arterial line for measurement of plasma [Na$^+$] by flame photometry, and the liver was freeze-clamped, weighed, and digested in nitric acid for measurement of hepatic tissue [Na$^+$]. The hepatic tissue water content was determined from the wet-to-dry weight ratio. pH$_i$ was calculated from the chemical shift of P$_i$ peak. [Mg$^{2+}$]$_{i, free}$ was estimated from the chemical shift of β-ATP resonance relative to the α-ATP peak, and by using a recently reported computer program that corrects all chemical shifts for changes in pH. Both methods gave nearly identical values of [Mg$^{2+}$]$_{i,free}$.

Before infusion of TmDOTP$^{5-}$, the mean arterial blood pressure (MAP) was 99±4 mm Hg for the sham burn group and 71±4 mm Hg for the burn group (P<0.05). After infusion of TmDOTP$^{5-}$, the MAP decreased to 78±3 in the sham burn group but to only 65±4 mm Hg in the burn group (p<0.05). Although the differences in MAP between the two groups were less after infusion of SR, the values remained significantly different (p<0.05). Throughout the study, heart rate averaged 261±19 beats/min and did not differ between groups.

Two series of $^{23}$Na NMR spectra collected from a control animal and from a burned animal collected during infusion of TmDOTP$^{5-}$ are shown in FIG. 5A and FIG. 5B. Infusion of SR resulted in a progressive increase in chemical shift difference between the Na$^+$ (i) and Na$^+$ (e) resonances. Once the Na$^+$ (i) resonance could be distinguished form the Na$^+$ (e) resonance, it did not change in amplitude with continued SR infusion in either group. This indicated that TmDOTP$^{5-}$ did not alter Na$^+$ (i) concentration in hepatic cells. The Na$^+$ (e) resonance increased in intensity somewhat during infusion of SR, but the small increase could be accounted for by the additional Na$^+$ counterions in the SR solution. A lower total dosage of TmDOTP$^{5-}$ was needed in burned animals (0.44±0.04 mmol) than in control animals (0.64±0.08 mmol) to produce an equivalent Na$^+$ shift. The $^{31}$P spectra of livers did not change appreciably during SR infusion in either group.

$^{23}$Na and $^{31}$P spectra of typical in vivo rat livers from burn and control groups are shown in FIGS. 6A–6B and FIGS. 6C–6D. The $^{23}$Na spectra show baseline resolved peaks from Na$^+$ (i) and Na$^+$ (e) in both groups. The $^{31}$P spectra were characteristic of liver studies: ATP, phosphodiesters, P$_i$, and phosphomonoesters were all detected without detection of phosphocreatine. There were quantitative differences in the $^{31}$P spectra between the burn and control groups as shown in Table 2. Burn injury caused a 30% decrease in hepatic ATP-to-P$_i$ concentration ratio (from 1.48 to 1.03). pH$_i$ in the sham burn group was 7.31 but was reduced to 7.21 in burned animals. Hepatic [Mg$^{2+}$]$_{i,free}$ was 577 μM in the sham burn group. After burn injury, [Mg$^{2+}$]$_{i, free}$ decreased to 415 μM.

Care was therefore taken to position the animal and the surface coil in the magnet, in tuning and matching the coil, and in setting the various instrument parameters. Consequently, MRS peak areas from different animals were compared. With these precautions, the standard error in the measurement of absolute $^{23}$Na resonance areas within a group of animals was <10%. The total Na$^+$ resonance area was the same in the two groups (7039 ±376 in sham burn control compared to 6988±519 in the burn group) after shift reagent infusion. This agreed with the total tissue Na$^+$ determined by flame photometry which was 35±2 meq/kg from the sham burn group and 32±2 meq/kg from the burn group.

Comparison of Na$^+$ (i) and Na$^+$ (e) resonance areas showed significant differences. The resonance area of Na$^+$ (e) from animals in the burn group was 4397±238 compared with 5641±293 in the sham burn group (P<0.05) and the area of Na$^+$ (i) from the burn group was 2591±286 compared with 1398±98 in the sham burn group (P<0.05). Both indices indicated that Na$^+$ moves into the liver cells of burned animals, likely accompanied by inward movement of water. Total hepatic tissue Na$^+$ and tissue water were not different between the two groups (Table 2).

TABLE 2

Hepatic Phosphates and Cations in Control and Burn Groups

|  | Sham Burn (n = 4) | Burn (n = 7) |
|---|---|---|
| NMR measurements | | |
| [ATP] / [P$_i$] | 1.48 ± 0.09 | 1.03 ± 0.04* |
| pH$_i$ | 7.31 ± 0.01 | 7.21 ± 0.02* |
| [Mg$^{2+}$]$_{i,free}$, μM | 577 ± 17 | 4115 ± 20* |
| [Na$^+$]$_i$ [Na$^+$]$_e$ | 0.25 ± 0.02 | 0.58 ± 0.03* |
| Chemical measurements | | |
| TWC, wet wt/dry wt | 3.19 ± 0.08 | 3.41 ± 0.09 |
| Plasma Na$^+$, meq/l | 153 ± 3 | 147 ± .6 |
| Tissue Na$^+$, meq/kg | 35 ± 2 | 32 ± 2 |

Values are means ±SD; n, no. of rats. NMR, nuclear magnetic resonance; [P$_i$], P$_i$ concentration; pH$_i$, intracellular ph; [Mg$^{2+}$]$_{i, free}$, intracellular free Mg$^{2+}$concentration; [Na$^+$]$_i$, intracellular Na$^+$ concentration; [Na$^+$]$_e$, extracellular Na$^+$ concentration; TWC, tissue water content. *Significantly different from control group (P<0.01).

As shown in Table 2, a dramatic increase in intracellular sodium ion in the liver was observed. In contrast, little change was measured in high energy phosphate levels. This demonstrated that the measurement of intracellular sodium ion increase in severe burn injury is useful for detecting adverse response of the liver to systemic injury.

EXAMPLE 3

The effect of ischemia on heart muscle is known to increase intracellular sodium ion concentration. It is expected that in vivo perfusion of heart tissue will provide results analogous to those observed with the burn injury model of Example 1; i.e., significant changes in levels of intracellular and extracellular sodium ion will be observed. Similar changes would also be expected for intracellular and extracellular potassium ion.

EXAMPLE 4

The ability to obtain baseline resolution of intra and extracellular sodium ion magnetic resonance spectra, as shown in the present invention, enables the creation of images of intra and extracellular sodium ion and images of relaxation times of sodium ion in either compartment. Such imaging employing frequency shift techniques are well known and can be found in numerous references, e.g., Brateman, L. *Am. J. Roentgenology* 146, 971 (1986) and Brown, T. R., Kincaid, B. M., Ugurvil, K. *Proc. Natl. Acad. Sci. U.S.A.* 79, 3523 (1982). Modern NMR techniques allow simultaneous determination of multiple spectra that convert selected peak areas from each volume element into image brightness. In phantom experiments, the inventors have produced selective sodium images.

EXAMPLE 5

Male Sprage-Dawley rats were prepared for magnetic resonance exam and TmDOTP$^{5-}$ was infused into animals as described in Example 2. TmDOTP$^{5-}$ produced well resolved $^{23}$Na resonances in the kidney with a separation of 7–10 ppm between the extra- and intracellular Na$^+$ resonances after infusion of about 0.681 mmoles of the SR per Kilogram of Body Weight (KgBW). The inventors also observed a third $^{23}$Na resonance, broader than the extracellular resonance and shifted to about 35 ppm. This is the first time this resonance has been observed in any SR aided experiment in any organ. After about 10 minutes of TmDOTP$^{5-}$ infusion (infusion dose 0.147 mmoles/KgBW), one broad shifted resonance became apparent at about 15 ppm. Continued infusion of the SR shifted this resonance further upfield. Simultaneously, another resonance became visible as a high frequency shoulder on the unshifted resonance after about 14 minutes of infusion (infusion dose 0.254 mmoles/KgBW). Finally, the three resonances became clearly resolved after about 17 minutes of infusion (infusion dose 0.334 mmoles/KgBW).

In comparison, infusion of DyTTHA$^{3-}$ did not produce resolved Na$^+$ resonances in the kidney in vivo. The single $^{23}$Na resonance broadened with infusion of this shift reagent and the intracellular Na$^+$ resonance became evident as a shoulder on the shifted extracellular Na$^+$ resonance only after 3–5 mmoles of DyTTHA$^{3-}$/KgBW had been infused. This SR dose was about 5–8 times higher than that required with TmDOTP$^{5-}$ to produce comparable shift. There was no indication of the existence of the third highly shifted Na$^+$ resonance.

$^{23}$Na spectra obtained from the analysis of the blood and urine samples collected during infusion of either TmDOTP$^{5-}$ or DyTTHA$^{3-}$ were compared with the respective in vivo kidney spectrum. The $^{23}$Na resonance from the blood sample was exactly coincident with the 7–10 ppm resonance in the kidney spectrum indicating that this in vivo resonance was of extracellular origin. The $^{23}$Na signal from the urine sample, on the other hand, was very close to the more shifted resonance in the in vivo kidney spectrum after TmDOTP$^{5-}$ infusion (FIG. 2A and FIG. 2B) suggesting that the latter originated from filtrate in the kidney. There was a signal from the urine sample at abut 35 ppm after infusion of DyTTHA$^{3-}$ also, though there was no distinguishable signal in the corresponding in vivo spectrum (FIG. 3A and FIG. 3B). This indicated that the urine signal actually existed but due to the extreme line broadening produced during DyTTHA$^{3-}$ infusion, it was lost in the baseline.

The infusion TmDOTP$^{5-}$ did not produce any change in $^{31}$P resonance areas or in the chemical shift of the metabolites. This indicated that cellular energy state and intracellular pH were unaffected by the SR. However, in some animals an increase in the linewidth of all $^{31}$P resonances was observed which may be attributed to the magnetic susceptibility and heterogenous distribution of the SR in the kidney. These data suggested that despite the small drop in blood pressure of the animals, the renal high energy phosphate levels were unaffected by TmDOTP$^{5-}$. Also, the $^{23}$Na spectra from in vivo kidney showed that once discernible from extracellular Na$^+$, the intracellular Na$^+$ resonance intensity does not change with further SR infusion, suggesting that transmembrane Na$^+$ transport is not disturbed by this SR.

Another measure of toxicity of a SR is its rate of washout from the system. It has been previously shown that induced chemical shift by a SR is directly proportional to its concentration. Therefore, by following the shift of the extracellular $^{23}$Na resonance once infusion is stopped, the inventors were able to determine the rate of washout of the R from the extracellular space. The data yielded a half-time of 8 to 10 minutes. The washout of TmDOTP$^{5-}$ was also observed from the $^{31}$P resonance of the phosphonate group of the DOTP. The data again yielded a half-time of 8 to 10 minutes.

While the methods of this invention have been described in terms of preferred embodiments, it will be apparent to those of skill in the art that variations may be applied to the methods and in the steps or in the sequence of steps of the methods described herein without departing from the concept, spirit and scope of the invention. More specifically, it will be apparent that potential applications of these methods include stroke and myocardial infarction where the proper course such as reperfusion therapy depends on a clinical judgement about the duration of ischemia and the severity of tissue injury. Other conditions such as mesenteric ischemia, diffuse cerebral injury due to hypoxia or ischemia, acute renal failure, toxic hepatic injury, acute limb ischemia are all contemplated to be conditions for which the disclosed methods may be employed. All such similar applications apparent to those skilled in the art are deemed to be within the scope, spirit and concept of the invention as defined by the appended claims. All claimed matter and methods can be made and executed without undue experimentation.

What is claimed is:

1. A magnetic resonance in vivo method of determining the ratio of intra- and extracellular sodium ions in tissue, comprising:

administering a non-sodium ion concentration perturbing dose of a calcium ion free
solution of TmDOTP$^{5-}$ to a mammal wherein said solution contacts a tissue in which determination of the ratio of intracellular and extracellular sodium ions is desired;

positioning a NMR coil near said tissue;
measuring $^{23}$Na peak areas of two resolved peaks that develop from split resonance of $^{23}$Na after infusion of said TmDOTP$^{-5}$ solution; and calculating a ratio of said peak areas wherein said ratio represents the ratio of the amounts of intra- and extracellular sodium ion.

2. The method of claim 1 wherein the administering is by infusion.

3. The method of claim 2 wherein the infusion is initiated at a slow rate for about 5–10 min before decreasing to a slower rate after a chemical shift difference of about 3–7 ppm between the intra- and extracellular sodium ion resonances is achieved.

4. The method of claim 3 wherein the infusion is initially at about 1–3 ml per hour.

5. The method of claim 3 wherein the initial infusion rate is increased to about 6–10 ml per hour over a period of about 5–10 min prior to achieving a chemical shift of about 3–7 ppm between the intra- and extracellular sodium ion resonances.

6. The method of claim 1 wherein the tissue contacted is identified as brain, liver, heart, lung, kidney or muscle.

7. A method of determining intracellular sodium ion tissue concentrations in vivo, comprising:
 (a) administering a non-sodium ion concentration perturbing dose of a calcium ion free solution of TmDOTP$^{5-}$ to a mammal;
 (b) positioning an NMR coil tuned to the frequency for $^{23}$Na$^+$ in a tissue where measurement is desired;
 (c) obtaining a ratio of $^{23}$Na peak areas from a $^{23}$Na NMR spectrum of intra- and extracellular sodium ion in said tissue under non-saturating conditions;
 (d) measuring intra- and extracellular volumes in said tissue and measuring extracellular sodium concentration in said tissue; and
 (e) calculating intracellular concentration of sodium ion from the ratio of intracellular to extracellular sodium ion, the extracellular and intracellular volumes of the tissue and the extracellular sodium concentration.

8. A magnetic resonance in vivo method of determining the ratio of intra-and extracellular potassium ion in tissue, comprising:
 administering a non-potassium ion concentration perturbing dose of a calcium ion free solution of TmDOTP$^{5-}$ to a mammal wherein said solution contacts a tissue in which determination of the ratio of intracellular and extracellular potassium ion is desired;
 positioning a NMR coil near said tissue;
 measuring $^{39}$K$^\pm$ peak areas of two resolved peaks that develop from split resonance of $^{39}$K$^\pm$ after infusion of said TmDOTP$^{5-}$ solution; and
 calculating a ratio of said peak areas wherein said ratio represents the ratio of the amounts of intra-and extracellular potassium ion.

* * * * *

UNITED STATES PATENT AND TRADEMARK OFFICE
CERTIFICATE OF CORRECTION

PATENT NO. : 5,951,473

DATED : September 14, 1999

INVENTOR(S) : A. Dean Sherry, Navin Bansel, Craig R. Malloy

It is certified that error appears in the above-identified patent and that said Letters Patent is hereby corrected as shown below:

On the title page:

Item #[75] delete "Bansal" and insert --Bansel--therefor.

Signed and Sealed this

Eighteenth Day of July, 2000

Attest:

Q. TODD DICKINSON

*Attesting Officer*  *Director of Patents and Trademarks*

UNITED STATES PATENT AND TRADEMARK OFFICE
CERTIFICATE OF CORRECTION

PATENT NO. : 5,951,473

DATED : September 14, 1999

INVENTOR(S) : A. Dean Sherry, Navin Bansal, Craig R. Malloy

It is certified that error appears in the above-identified patent and that said Letters Patent is hereby corrected as shown below:

On the title page:

Item #[75] delete "Bansel" and insert --Bansal--therefor.

Signed and Sealed this

Nineteenth Day of December, 2000

Attest:

Q. TODD DICKINSON

*Attesting Officer*            *Commissioner of Patents and Trademarks*